United States Patent [19]

Urdal et al.

[11] Patent Number: 4,578,335
[45] Date of Patent: Mar. 25, 1986

[54] INTERLEUKIN 2 RECEPTOR

[75] Inventors: David L. Urdal; Carl J. March; Steven K. Dower, all of Seattle, Wash.

[73] Assignee: Immunex Corporation, Seattle, Wash.

[21] Appl. No.: 612,559

[22] Filed: May 21, 1984

[51] Int. Cl.[4] .................. C12P 21/00; C07K 3/02
[52] U.S. Cl. ..................... 435/68; 435/240; 435/241; 435/948; 260/112 R; 260/112.5 R
[58] Field of Search ............ 260/112 R, 112.5 R; 435/68, 70, 240, 241, 948

[56] References Cited

U.S. PATENT DOCUMENTS 4,377,482  3/1983  Rivier .................. 260/112.5 R
4,411,993  10/1983  Gillis .................. 435/68

OTHER PUBLICATIONS

Third International Lymphokine Workshop: *Cell Immunol* (70) 1982, pp. 380–409, (only part of reference submitted–pertinent part).

Summary of Third International Lymphokine Workshop; *Lymphokine Res.* 1(3), 1982.

Smith et al. *J. Immunol* 131(4), 1983, Production and Characterization of MAB . . . Tactics, p. 1808.

Leonard et al., *Nature* (300), 1982, p. 267, A Monoclonal Antibody that Appears to Recognize the Receptor for Human T-Cell . . . Receptor.

Robb et al., *J. Exp. Med.* (158), 1983, p. 1332, Direct Demonstration of the Identity of T-Cell Growth Factor Binding . . . Antigen.

*Primary Examiner*—John Kight
*Assistant Examiner*—Garnette D. Draper
*Attorney, Agent, or Firm*—Christensen, O'Connor, Johnson & Kindness

[57] ABSTRACT

Interleukin-2 receptor derived from normal and malignant cells has been purified by use of various techniques including affinity chromatography in conjunction with a monoclonal antibody directed to the receptor. Purification also involved reversed phased high performance liquid chromatography. By these techniques, interleukin-2 receptor has been purified to homogeneity. The high purification of the interleukin-2 receptor has enabled this protein molecule to be partially sequenced.

10 Claims, No Drawings

INTERLEUKIN 2 RECEPTOR

TECHNICAL FIELD

The present invention relates to interleukin 2 receptor, and more particularly to purified interleukin 2 receptor derived from normal and malignant cells and a process for producing same.

BACKGROUND OF THE INVENTION

The success of many normal immune responses require the participation of T-cells. The proliferation of T-cells to sufficiently large numbers to enable them to assume an effective role in immune responses is controlled by the presence of the polypeptide growth hormone interleukin 2 (hereinafter "IL-2"), formerly known in the literature as "T-cell growth factor" or "TCGF." Gillis and Smith, 28 Nature 154 (1977). The mechanism by which IL-2 controls the growth of T-cells is not completely understood. However, it is known that IL-2 acts on T-cells via a specific, high affinity plasma membrane receptor. Also, in order to continue to divide, IL-2 dependent T-cells must express this receptor and IL-2 must bind to a portion of this receptor. Robb et al., 154 J. Exp. Med. 1455 (1981). A more complete knowledge of the biochemistry of the IL-2 receptor would foster a better understanding of the interaction between IL-2 and T-cells. To date, this has been hampered, at least in part, by the unavailability of IL-2 receptor in purified form.

Leonard et al., 300 Nature (London) 267 (November 1982), reported employing a murine monoclonal antibody, designated as anti-Tac, to significantly block the binding of radiolabelled IL-2 to the human lymphoma T-cell line, HUT-102. This antibody resulted from the immunization of mice with long term cultures of human T-cells. The anti-Tac antibody was reported as binding to a glyco-protein receptor having a molecular weight of about 47,000–53,000 daltons and also to proteins having molecular weights of about 113,000 and 180,000 daltons. Leonard et al. hypothesized, but did not establish, that the cell surface determinant (i.e., the 47,000–53,000 molecular weight protein) to which the anti-Tac antibody bounded to was the IL-2 receptor.

Robb and Green, 158 J. Exp. Med. 1332 (1983), reported employing the anti-Tac antibody in conjunction with mitogen-activated normal lymphocytes to immunoprecipitate a protein having a molecular weight of about 52,000–57,000 daltons. They found that this same protein also bound to IL-2. These researchers opined that this reactive molecule contained the binding site for IL-2 for normal lymphocytes.

Leonard et al., 80 Proc. Natl. Acad. Sci. (U.S.A.) 6957 (1983) observed that receptors recognized by anti-Tac antibody on HUT-102 cells and on phytohemaggelutinin-activated normal T-cells appear to be larger on reducing gels than on nonreducing gels, thus suggesting the presence of intrachain disufide bonds. Also, the HUT-102 cell receptor was reported to exhibit an isoelectric point of from 5.5 to 6.0. From post-translational studies Leonard et al. suggested that the HUT-102 receptor is composed of a peptide backbone of 33,000 molecular weight that is initially glycosylated by an N-linked mechanism to achieve a 35,000–37,000 molecular weight doublet and then glycosylated by an O-linked mechanism to increase the weight of the molecule by about 13,000–15,000 datons. Although the researchers stated that their studies "suggested" that the HUT-102 cell receptor recognized by the anti-Tac antibody is the human receptor for IL-2, they admitted that actual proof would require purifying the receptor, which prior to the making of the present invention had not been accomplished.

DETAILED DESCRIPTION

The present invention relates to the production of IL-2 receptor derived from malignant and normal T-cells, to the purification of the IL-2 receptor to homogeneity and to the determination of the amino acid sequence of the amino terminal portion of the IL-2 receptor molecule. The IL-2 receptor of the present invention is purified by a combination of affinity chromatography and reversed phased high performance liquid chromatography. The affinity chromatography procedure employs a highly specific monoclonal antibody that recognizes an epitope on the receptor molecule. Once purified to homogenity, the amino acid sequence of the amino terminal portion of the receptor molecule can be ascertained by use of a protein sequencer.

PREPARATION OF IL-2 RECEPTOR EXTRACTS FROM MALIGNANT AND NORMAL CELLS

Malignant cells are cultured in vitro in a suitable culture medium supplemented with serum and various additives. After an optimum culture period, the cells are harvested and IL-2 receptor containing extracts formed from the cells. The malignant cell lines which may be employed as a source of IL-2 receptors include T-lymphoma or T-leukemia cell lines. These cell lines are produced by either a spontaneous occurrence, via viral transformation or via transformation by chemical carcinogen or irradiation. The present invention has been carried out in conjunction with a naturally occurring lymphoma cell line, designated as HUT-102. The cell line is available from a wide variety of sources and has been used extensively by researchers.

The present invention also includes producing IL-2 receptor molecules from normal cells. For instance, human peripheral blood mononuclear cells are separated from human blood by Ficoll-Hypaque centrifugation as described by Boyum, 18 Scand. J. Clin. Lab. Invest. Suppl. 77 (1966). Adherent cells are removed by plastic adherence and then cultured in vitro in serum containing medium in the presence of an activating agent, such as a T-cell mitogen. After a suitable period of time, the cells are harvested by centrifugation. Examples of T-cell mitogens that may be used as activating agents, include phytohem-agglutinin ("PHA"), concanavalin A ("Con A") or pokeweed mitogen ("PKM").

The numbers IL-2 receptors expressed by stimulation of the peripheral blood leukocytes with a plant mitogen varies with time. Optimum levels of IL-2 receptor expression are reached at approximately 72 hours after mitogen stimulation.

The culture medium used to expand the IL-2 receptor bearing malignant and normal cells may consist of commercially available medium, such as Roswell Park Memorial Institute ("RPMI") medium. Dulbecco's Modified Eagle Medium ("DMEM") and Click's Medium. Additives, which may be individually or in combination added to the culture medium, include serum, such as fetal calf serum ("FCS") or normal human serum. Additional additives include glutamine and various antibiotics, such as penicillin and streptomycin.

The process of culturing the malignant and normal cells to induce receptor formation may be carried out in various environmental conditions. Preferably, however, the cultures are maintained in the temperature range of approximately 35°–38° C. in a humidified atmosphere of approximately 5–10% $CO_2$ in air. Also, the pH of the culture should be kept in slighty alkaline condition, in the range of approximately pH 7.0–7.4.

IL-2 receptor containing extracts are prepared from the cultivated normal and malignant cells by harvesting the cells by centrifugation. The cells are then washed with a buffered saline solution and resuspended in the buffered saline solution together with a detergent and phenylmethylsulfonylfluoride ("PMSF"). After a period of time the detergent extract is centrifuged to remove nuclei and insoluble debris and then is stored frozen until used.

PREPARATION OF MONOCLONAL ANTIBODY AGAINST IL-2 RECEPTOR

The present invention also concerns the production of a monoclonal antibody having a high affinity to an epitope on the IL-2 receptor molecule. The antibody is used as a bound ligand in the affinity chromatography procedures during purification of the IL-2 receptor. The antibody is also employed in a radioimmune precipitation assay and in soluble receptor assays to monitor the IL-2 receptor protein during purification steps, as more fully discussed below.

A preferred procedure for generating the monoclonal antibody against the IL-2 receptor is generally disclosed in U.S. Pat. No. 4,411,993, incorporated herein by reference. In the procedure, BALB/c mice are injected with PHA activated human peripheral blood leukocytes ("PHA/PBL") several times at weekly intervals. Prior to the first injection, the PHA/PBL is emulsified in complete Freund's adjuvant and prior to the remainder of the injections the PHA/PBL is emulsified in incomplete Freund's adjuvant.

During the course of immunization, serum samples from the mice are tested by an enzyme linked immunoabsorbant assay ("ELISA"), as is well known in the art, for the presence of antibody reaction with the immunization cells. Once an antibody titer is detected, the animals are given an intravenous injection of PHA/PBL suspended in saline. Several days later the animals are sacrificed and their spleens harvested. Single cell suspensions from the splenocytes are cultured in tissue culture medium supplemented with various additives to expand the number of antibody producing cells. The antibody producing cells are isolated from the culture and purified by standard techniques for subsequent fusion with myeloma cells to produce hybrid cells that express anti-IL-2 receptor antibody. The fusion process is detailed in U.S. Pat. No. 4,411,933 and in Nowinski et al., 93 *Virology* 111 (1979), incorporated herein by reference.

After fusion, the hybrid cells are resuspended in a tissue culture medium supplemented with various additives and selected suppressing agents to preclude the growth of unfused myeloma cells, double myeloma cells, unfused spleen cells and double spleen cell hybrids, thereby liberating the anti-IL-2 receptor antibody producing cells. Such growth inhibitors or suppressants may include hypoxanthine, aminopterin and thymidine (hereinafter collectively referred to as "HAT").

After several days of culture, the hybridoma cells, which are generated, are screened by ELISA assay for anti-IL-2 receptor antibody responses. These hybrid cells are tested for production of antibody capable of inhibiting both mitogen and antigen induced proliferation of human peripheral blood leukocytes. The hybrid cells which give positive ELISA results are gradually weaned to HAT-free medium and then cultured in vitro in large volumes for bulk production of antibody. Alternatively, the cells may be expanded in vivo by injecting the hybridoma cells in the peritoneal cavities of mice and thereafter collecting the intraperitoneal ascites which contain high concentrations of the antibody. The antibodies contained in the ascites fluid can be isolated and concentrated by established techniques, such as by ammonium sulfate precipitation followed by gel column chromatography. If required, the antibody can be further purified by ion exchanger chromatography and/or affinity chromatography. By the above process, a particular hybridoma, designated as 2A3, was found to produce antibody that significantly inhibited both mitogen and antigen induced proliferation of human peripheral blood leukocytes.

The present invention also includes identifying potent cell line sources of anti-IL-2 receptor antibody by cloning cell lines known to produce this antibody, for instance, the 2A3 cell line. The cloning is accomplished by the limiting dilution procedure, as is well known in the art and as is detailed in U.S. Pat. No. 4,411,993. By this procedure, one particular subclone, designated as 2A3-A1H was found to produce antibody that substantially entirely inhibited both mitogen and antigen induced proliferation of human peripheral blood leukocytes. The 2A3-A1H antibody has been characterized as of the $\gamma_1 K$ isotype with an unusually high affinity to the human IL-2 receptor.

A control antibody preferably is employed to confirm the processes of the present invention utilizing anti-IL-2 receptor antibody and as a reagent in the purification of the receptor. The control antibody should be of the same isotype as the anti-IL-2 receptor antibody. Applicants have identified the antibody secreted by the mouse myeloma cell line MOPC-21 as a suitable control antibody for the 2A3-A1H antibody. The MOPC-21 cell line is widely available from numerous private and commercial sources.

SOLUBLE IL-2 RECEPTOR ASSAYS

Assays employing the 2A3-A1H monoclonal antibody are used in conjunction with the present invention to monitor the quantitative amount of IL-2 receptor present in the initial cell lysates and during purification procedures. These assays hinge on the discovery by applicants that the 2A3-A1H antibody has an extremely high affinity for the IL-2 receptor, the affinity constant being in excess of $5 \times 10^9$ per $M^{-1}$ and that the 2A3-A1H antibody can be radioiodinated to high specific activity and still retain its capacity to bind to the IL-2 receptor.

One such perferred assay involves ascertaining the extent to which samples of cell lysate or column chromatography fractions containing IL-2 receptors are capable of inhibiting the binding of radiolabelled IL-2 antibody to glutaraldehyde fixed, intact receptor bearing cells. This assay relies on the observation by applicants that IL-2 receptor is stable to glutaraldehyde fixation, i.e., the receptor cannot be extracted from such cells with nonionic detergents, such as Triton X-100, and the presence of detergent does not affect the binding of radiolabelled 2A3-A1H antibody to the fixed cells. Preincubation of a subsaturating dose of iodinated 2A3-A1H antibody with detergent solutions containing the IL-2 receptor inhibits the subsequent binding of the 2A3-A1H antibody to the glutaraldehyde fixed cells. This assay will hereinafter be referred to as the "soluble inhibition assay."

For use in the soluble inhibition assay, the 2A3-A1H antibody is radiolabeled with iodine 125 ("$^{125}$I") by a chloramine-T method, as is well known in the art and as described by Segal and Hurwitz, 118 *J. Immunol.* 1338 (1977). The standard labeling conditions employed are: 50 ug 2A3-A1H IgG; 4 nmoles of chloramine-T (Sigma Chemical Company, St. Louis, Mo.; and, 2.5 mCi of $^{125}$I sodium iodide (New England Nuclear, Boston, Mass.), in a final volume of 60 ul. This protocol has resulted in preparations of $^{125}$I-2A3-A1H, which routinely have specific activities in the range of 2 to $5 \times 10^{15}$ cpm/mmole ($1.3-3.3 \times 10^7$ cpm/ug). Also, 2A3-A1H antibodies labeled in this way were found to be more than 95 percent bindable to IL-2 receptor bearing cells and had apparent affinity constants in excess of $5 \times 10^9 M^{-1}$.

In the soluble inhibition assay, 50 ul of $^{125}$I-2A3-A1H($2 \times 10^{-10}$M) is mixed with 50 ul of an appropriate dilution of cell lysate or column fraction in phosphate buffered saline ("PBS") containing 1% (w/v) Triton X-100 detergent (Sigma Chemical Company, St. Louis, Mo.) in RPMI - 1640 medium containing 2% bovine serum albumin ("BSA"), 20 mM HEPES buffer (pH 2.7) and 0.2% sodium azide ("NaN$_3$") (collectively "binding medium"). This mixture is incubated for one hour at room temperature in round bottom 96 well plates (Linbro, Hamden, Conn.). At the end of the incubation period, $10^7$ glutaraldehyde fixed, PHA activated human T-cells in 50 ul of binding medium are added to detect uncomplexed $^{125}$I-2A3-A1H. Incubation is continued for one hour at room temperature. Duplicate 60 ul aliquots of the mixture are then transferred to precooled 400 ul polyethylene centrifuge tubes containing 200 ul of a phthalate oil mixture and the cell bound antibody is separated from unbound antibody by centrifugation. The details of the well-known phthalate oil separation method are set forth in Segal and Hurwitz, supra. The percent of specific inhibition caused by the lysate or column fraction is calculated by using 50 ul of PBS-2% Triton X-100 instead of a test sample for the positive control. Also, 15 ul of PBS-2% Triton X-100 containing $10^{-8}$M unlabeled 2A3-A1H is used as a negative control.

The nitrocellulose dot assay ("dot assay") is used as a second soluble IL-2 receptor assay to quantify the amount of IL-2 receptor molecules present in a sample of cell lysate or column fraction. Briefly, in the dot assay, solutions are made of a log$_2$ dilution series of potential IL-2 receptor containing samples and PBS containing 1% Triton X-100. Samples of 5 ul of these solutions are then applied to a piece of dry nitrocellulose (Schleicher and Schvell, Keene, N.H.). The nitrocellulose is then blocked by overnight incubation in 10 ml of 0.5 M TRIS, (ph 7.5), 0.15 M NaCl, 3% BSA (hereinafter TBS-3% BSA). After the blocking step, the nitrocellulose is incubated for one hour at room temperature in 10 ml of TBS-3% BSA containing 0.05 ug/ml $^{125}$I - 2A3-A1H and 0.6 ug/ml unlabeled MOPC-21. The nitrocellulose is then washed three times in TRIS buffered saline and twice in TRIS buffered saline containing 1% (w/v) Nonidet P-40 detergent (Gollaro Schlesinger Chemical Manufacturing Corp., Carle Place N.Y.), 1% (w/v) sodium deoxycholate, and 0.1% (w/v) sodium lauryl sulfate. Each of these washes lasts 30 minutes at room temperature. After the final wash, the nitrocellulose sheet is blotted dry, covered with a clear plastic sheet and then exposed at $-70°$ C. to Kodak X-omat AR ® film.

RADIOIMMUNE PRECIPITATION ASSAY

The specificity of the IL-2 receptor antibody is ascertained with a radioimmune precipitation assay involving forming precipitations between samples of radiolabeled IL-2 receptor molecules and an antibody to the receptor and then employing polyacrylamide gel electrophoresis and either fluorography or autoradiography to visualize the receptor proteins that were precipitated. In this assay technique, the IL-2 receptor molecules are labeled either by surface iodination after extraction or metabolically before extraction.

Radiolabeling of the IL-2 receptor cell membranes after extraction is performed by the $^{125}$I-IODO-GEN method (Pierce Cl. Co., Rockford, Ill.). The details of this radiolabeling technique are well known in the art and described by Urdal et al., 1 *Cancer Metastasis Reviews* 65 (1982); and, Markwell et al., 17 *Biochemistry (Wash.)* 4807 (1978). The use of $^{35}$S methionine to label the receptor molecules metabolically also is well known in the art and is described by, for instance, Robb and Greene, 158 *J. Exp. Med.* 1332 (1983).

After labeling with $^{125}$I or $^{35}$S methionine, the cells are washed with PBS and then extracted with PBS containing 1% Triton X-100 and 2 mM PMSF. Affinity supports for the radioimmune precipitation assay are prepared by coupling purified antibodies (2A3-A1H and MOPC-21) to Affi-gel-10. Briefly, one volume of moist Affi-gel-10 is added to one volume of antibody (3-5 mg/ml) in borate buffered saline ("BBS") and then the mixture incubated overnight at $4°$ C. Thereafter, 100 ul of 1 M glycine ethylester is added per ml of gel to couple any of the unreacted groups in the Affi-gel-10. Applicants have found that routinely from 3 to 4 mg of antibody are coupled per ml of the gel. Before use, each gel is washed extensively with PBS. Each gel is also washed with a buffer solution composed of PBS-1% Triton X-100 and 0.5 M TRIS, pH 7.5, containing 0.5 M NaCl, 1% (w/v) NP 40 detergent, 1% (w/v) sodium deoxycholate, and 0.1% sodium dodecyl sulfate ("SDS") (collectively "RIPA buffer").

The radioimmune precipitations are performed by mixing 50 ul of radiolabeled cell extract with 75 ul of PBS-1% percent Triton X-100 containing 20% (v/v) of affinity gel having antibody coupled thereto. The mixture is incubated over night at $4°$ C. and then the gel washed four times with RIPA buffer and twice with 0.1 M TRIS, ph 8.0, containing 0.5 M NaCl, 5 mM, ethylene diamine tetra acetate ("EDTA"), and 0.5% NP-40 detergent. After the final wash, the resulting gel pellets are suspended in 40 ul of SDS polyacrylamide gel sample buffer (0.06 M TRIS, ph 6.8, 2% SDS, 10% glycerol, 5% 2-mercaptoethanol and boiled for three minutes to break apart the bonds between the antibody and the IL-2 receptor molecules. A 30 ul sample of the supernate is then analyzed by SDS-polyacrylamide gel electrophoresis (PAGE) (8% polyacrylamide gel for $^{125}$I labeled receptor; 12% polyacrylamide gel for $^{35}$S methionine labeled receptor) according to the stacking gel procedure of Laemmli, 227 *Nature (London)* 680 (1970).

In the lysate analysis the receptor proteins employing the $^{35}$S methionine gels are visualized by fluorography. To this end, the $^{35}$S methionine gels were impregnated with Enhance (New England Nuclear, Boston, Mass.) prior to drying and fluorography. The receptor proteins immunoprecipitated with the $^{125}$I gels are visualized by autoradiography. To this end, the $^{125}$I gels are stained with Coomassie blue prior to drying and autioradiography. Both the $^{35}$S methionine and $^{125}$I gels are exposed to Kodak X-omat AR ® film at $-70°$ C. for 24 to 72 hours.

GEL ELECTROPHORESIS OF CHROMATOGRAPHY COLUMN FRACTIONS

Fractions eluted from the affinity chromatography and reversed phase HPLC columns employed in the purification processes of the present invention are assayed by gel electrophoresis. 50 ul aliquots were removed from the eluate fractions. The aliquots are dried under vacuum after addition of 2 ul of 10% SDS (w/v) to each aliquot. The dried residue is dissolved in 40 ul of SDS polyacrylamide gel sample buffer and then boiled for 3 minutes. The solution is applied to an 8% polyacrylamide gel and electrophoresis is then carried out by the stacking gel procedure of Laemmli, supra. The resulting gel samples are silver stained by the method described by Oakley et al., 105 *Anal. Biochem.* 361 (1980).

PURIFICATION OF IL-2 RECEPTOR

Cell extracts from the malignant and normal cells produced by the above procedures are initially concentrated by affinity chromatography techniques employing the same affinity supports used in the radioimmune precipitation assay described above. The procedure employed involves applying cell extracts first to an MOPC-21 column and then to a second column prepared with a mixture of MOPC-21 antibody and 2A3-A1H antibody so that in the second column from 3 to 4 mg of total IgG is coupled to each ml of gel, but only 10 to 30% of the antibody is composd of 2A3-A1H. This technique is used to counteract the extremely high affinity between the 2A3-A1H antibody and the IL-2 receptor.

In the purification procedure, the cell extracts, as prepared above, are first applied to the MOPC-21 column that has been preequilabrated with an appropriate buffer containing a detergent, thereby to remove proteins in the cell extract that might nonspecifically bind to mouse immunoglobulin. The flow through from the MOPC-21 column is then applied to the 2A3-A1H column. Elution is carried out with an appropriate saline-detergent solution. The recovered fractions are then dialyzed against decreasing concentrations of the eluting agent to optimize the recovery of biological activity.

Fractions are collected and assayed by gel electrophoresis and silver staining, as described above. Applicants have found that by use of the affinity chromotography procedure, IL-2 receptor from malignant cells which constitutively produce the receptor is purified approximately 1600 times from initial cell lysate. A somewhat lower purification level is typically attained for IL-2 receptor from activated normal cells.

The pooled active fractions from the above affinity chromotography procedure is employed as a starting material for the HPLC procedures. The HPLC technique used in the present invention preferably employs a reversed phase, tetra methyl bonded silica column having a pore size sufficiently large to be optimumly utilized with the proteineaceous IL-2 receptor, i.e., a pore size of at least 300 Å.

Suitable reversed phased HPLC columns for use in the practice of the present invention are articles of commerce. A preferred column for this purpose is the Vydac C-4 reversed phase column commercially available from Separations Groups, Hesperia, Calif. This column consists of tetra methyl silane groups covalently bonded by means of a siloxane (silicon-oxygen-silicon) bond to the surface of the 300 Å pore diameter silica gel which has been classified to a mean particle size of 5 microns.

The elution of the proteins from the HPLC column is carried out in a manner well known in the art. A suitable elution procedure for removing the bonded receptor molecule proteins from the tetra methyl column involves the use of a linear gradient of acetonitrile. A preferred gradient for this purpose is 0 to 5 percent (v/v) acetonitrile gradient in trifluoroacetic acid (TFA), pH 2.1.

The eluted protein can be conveniently monitored with detection systems that are well-known in the art. For example, an automated fluorescence detection system as described by Stein and Moschera, 78 *Method Enzymol.*, 435 (1981), may be employed. Alternatively, the relative protein concentration in the fractions eluted from the HPLC columns can be determined by measuring absorbance of the eluded material in an automated ultraviolet light spectrophotometer, at 214 nanometers light wave length. The suitable automated ultraviolet light absorbance detection apparatus is available from Waters Associates, Millford, Mass.

By use of the above described soluble receptor assay techniques, applicants have found that the specific activity of the IL-2 receptor after HPLC purification is very high, i.e., approximately 21,000 femtomole ("fm") IL-2 receptor/ug protein for IL-2 receptor derived from malignant cells. This is approximately a 16,700 fold level of purification over the specific activity of the IL-2 receptor in the starting cell lysate. The specific activity of the IL-2 receptor from normal T-cells was about ⅓ of the specific activity from malignant cells. By polyacrylamide gel electrophoresis and silver staining, applicants ascertained that the molecular weight of the IL-2 receptor from normal cells is approximately 60,000 daltons, as opposed to 55,000 daltons for receptor molecules found constitutively on the malignant cells.

AMINO ACID SEQUENCING

The ability to prepare homogeneous IL-2 receptor has permitted applicants to determine the amino acid composition and sequence of the amino terminal portion of this molecule. This information may be employed to assist in the cloning of the IL-2 receptor gene and the production of large quantities of pure IL-2 receptor for clinical trials and ultimately for widespread medical use. Moreover, the availability of homogeneous IL-2 receptor will no doubt lead to a more complete understanding of the biology of IL-2. While the prior art has said to have partially "characterized" the IL-2 receptor, applicants are not aware of any instances in which this protein has been truly purified to homogeneity to the extent that the receptor can be analyzed for amino acid composition and sequence.

Samples of homogeneous IL-2 receptor, as prepared above, can be analyzed for amino acid composition and sequence, for instance with an automated sequencer, such as with an Applied Biosystems model 470A protein sequencer. Ideally, several sequencing runs are made to confirm the accuracy of the sequence. Through this technique, appliants have found that the first 15 residues of the amino terminal portion of the IL-2 receptor molecule are composed of the following sequence: Glu-Leu-Cys-Asp-Asp-Asp-Pro-Pro-Glu-Ile-Pro-His-Ala-Thr-Phe.

The processes and products of the present invention are further illustrated by the following examples.

EXAMPLE 1

Preparation of IL-2 Receptor Containing Extracts From Malignant Cell Line

Hut-102 cells in a concentration of $2 \times 10^5$ cells per ml are cultured in 100–500 ml volumes in various plastic culture flasks or bottles (Falcon Plastics, Oxnard, Calif.) in RPMI-1640 medium. The medium is supplemented with 10% FCS, 2 mm glutamine, 100 U/ml penicillin and 100 ug/ml streptomycin. Since the HUT-102 cells have been reported to produce human T-cell leukemia virus (HTLV-1), work with this cell line is performed in a P-3 isolation facility.

The cells are cultured for 3–5 days in a humidified atmosphere of 5% $CO_2$ in air. After this period of time, viable cells are harvested by centrifugation and washed three times in PBS. Thereafter, the cell pellet is suspended in a volume that is three times the volume of the cell pellet n a solution composed of PBS containing 1% (w/v) Triton X-100 detergent and 2 Mm PMSF. This mixture is kept on ice and periodically vortexed for 30 minutes. The extract was then centrifuged at $20,000 \times g$ for 20 minutes to remove nuclei and insoluable debris. The cell extract, as thus prepared, is then stored at $-70°$ C. until used.

EXAMPLE 2

Preparation of IL-2 Receptor Containing Extracts From Lectin Activated Normal Cells Human peripheral blood mononuclear cells are prepared by Ficoll-Hypaque density gradient centrifugation as described by Boyum, supra. Briefly, enriched T-cells are obtained by rosetting with neuraminidase-treated sheep erythrocytes. The resulting rosetting (E+) and nonrosetting (E−) cells are incubated separately in 100-mm plastic petri dishes in 8% FCS at a concentration of $2-5 \times 10^6$ per ml. The adherent E− to cells are recovered with a rubber policeman after removing nonadherent cells with three media washes. The E− adherent cells together with the E+ to nonadherent cells in a radio of 1:25 are placed in bulk culture in 75-$cm^2$ flasks at a concentration of about $1-2 \times 10^6$ cells/ml in RPMI-1640 medium supplemented with 10% FCS, 100 U/ml penicillin and 100 ug/ml streptomycin. Activation is accomplished with 1% (v/v) PHA (Difco Laboratories, Detroit, Mich.). The cultures are incubated at 37° C. in an humified atmosphere of 5% $CO_2$ in air. Aliquots containing approximately $1-2 \times 10^7$ cells are removed at various times for analysis of cell surface IL-2 receptors.

Cells are harvested by centrifugation approximately 72 hours after mitogen stimulation, and washed three times with PBS. The resulting cell pellet is suspended in a volume three times the volume of the pellet in a solution composed of PBS containing 1% (w/v) triton X-100 detergent and 2 mM PMSF. The resulting mixture is kept on ice with periodic vortexing for 30 minutes. Thereafter, the extract is centrifuged at $20,000 \times g$ for 20 minutes to remove nuclei and insoluable debris. The resulting cell extracts are stored at $-70°$ C. centrigrade until used.

EXAMPLE 3

Production of Monoclonal Antibody To IL-2 Receptor

Female BALB/c (Jackson Laboratories, Bar Harbor, Me.) of ages of from 8–12 weeks are immunized intradermally in the hind legs with $10^7$ PHA/PBL. Prior to immunization, the PHA/PBL cells are prepared as an emulsion by mixing these cells with 0.4 ml of complete Freund's adjuvant (Difco Laboratories, Detroit, Mich.). After the initial immunization, the mice are rechallenged weekly for four weeks with $10^7$ PHA/PBA in incomplete Freund's adjuvant.

Periodically, serum from the mice is collected and tested individually for binding to PHA/PBL by ELISA, in a manner well known in the art. The animals found to have the highest response are given an additional intravenous injection of $10^7$ PHA/PBL in PBS. Four days later, the animals are sacrificed by cervical dislocation. The spleens of the animals are harvested and single cell suspensions prepared therefrom. The spleen cells are cultured in medium.

Fusion is achieved by mixing approximately $20 \times 10^6$ spleen cells with approximately $10 \times 10^6$ NS-1 murine myeloma cells in a 50 ml conical centrifuge tube. The cell mixture is pelleted by centrifugation for 5 minutes at $200 \times g$, and then the supernate removed by aspiration. The centrifuge tube with its intact cell pellet is transferred into a 37° C. water bath. Then polyethylene glycol 15 w (Eastman, Inc.) (50% (w/v) in RPMI-1640 is added to the cell pellet in dropwise manner at a ratio of 1 ml of PEG/$1.6 \times 10^8$ spleen cells. Thereafter, one volume of RPMI-1640 and 10 volumes RPMI 1640 containing 15% FCS and 1 mM pyruvate are slowly added during gentle stirring. Then, the cell suspension is centrifuged at $200 \times g$ for 5 minutes and the supernate discarded to complete the fusion process.

The hybrid cells are selected by resuspending the resulting cell pellet in Click's medium containing 15% FCS and 100 mM sodium pyrvate. The unfused myeloma driver cells (NS-1), double NS-1 hybrids, unfused spleen cells and double spleen cell hybrids are prevented from proliferation by the addition to the medium of approximately 13.6 mg/L of hypoxanthene, 0.176 mg/L aminopeterin and 3.88 mg/L of thymidine. The suspension is then divided into 200 ul aliquots in a flat-bottom microliter plates (No. 3596, Costar Inc., Cambridge, Mass.). The cultures are maintained at approximately 37° in a humidified atmosphere of 5% $CO_2$ in air.

After 10 days of culture, a 100 ul aliquot of supernate is removed from each viable culture and tested in an ELISA assay for binding to PHA/PBL (IL-2 receptor positive) or PBL (IL-2 receptor negative). Hybrids which demonstrate significant binding to PHA/PBL and little or no binding to PBL are transferred to 1 ml cultures and gradually weaned to HAT-free media. These hybrids are subcloned by limiting dilution cultures. Through this process, applicants have identified one particular hybrid clone, designated at 2A3-A1H, which significantly inhibits both mitogen and antigen induced proliferation of human PBL. Samples of this cell line are on deposit with the American Type Culture Collection, Rockville, Md., under accession No. HB 8555. The 2A3-A1H monoclonal antibody has been characterized as of the $\gamma_1$K isotype that exhibits a very high affinity to the human IL-2 receptor. This antibody inhibits the binding of IL-2 to its receptor and is antagonistic of IL-2 action.

EXAMPLE 4

In Vivo Production of Hybridoma Cells Producing Monoclonal Anti-IL-2 Receptor Antibodies Anti-IL-2 receptor antibody was produced in high concentration in vivo by intraperitoneal injection of BALB/c mice with approximately $1-10 \times 10^6$ hybridoma cells. One week prior to hybridoma cell injection, recipient BALB/c mice were given approximately 1.0 ml of pristane intraperitoneally as an ascites inducing irritant. From 8 to 14 days after hybridoma injection, intraperitoneal ascites are collected and each volume of fluid is mixed with 0.9 volume of 45% saturated ammonium sulfate and stirred overnight. The precipitate is separated by centrifugation and redissolved in phosphate buffer (0.05 M), pH 6.8. Residual ammonium sulfate is removed by dialysis against the same buffer.

The protein solution is then passed over a 5 ml bed volume DE-52 column (Whatman, Clifton, N.J.) and the fronting peak of protein is pooled. The pooled fractions are dialyzed against 0.02 M sodium borate, 0.1 M sodium NaCl, pH 8.5 ("BBS") and then applied to a 2.6×90 cm ACA-34 (LKB, Bromma, Sweden) gel filtration column previously equilibrated in the same buffer. The fractions corresponding to IgG are collected and pooled. Yields typically are in the range of 3 mg IgG/ml of ascites.

EXAMPLE 5

Purification of IL-2 Receptor By Affinity Chromatography

Cell extracts from normal and malignant cells produced by the procedures of Examples 2 and 3 are concentrated by affinity chromatography technique employing an initial gel column having control antibody for removing protein that might nonspecifically bind to mouse IgG and a second column having 2A3-A1H antibody bound thereto. The control antibody used in the initial column is secreted by the myeloma cell line MOPC-21. This antibody is of the same isotype as the 2A3-A1H antibody and is readily available.

To prepare the columns, purified 2A3-A1H and MOPC-21 antibodies are cupled to Affi-gel-10 (Biorad, Richmond, Calif.) according to the manufacturer's instructions. Equal volumes of moist Affi-gel-10 and antibody (3-5 mg/ml) in PBS are mixed together and incubated overnight at 4° C. Thereafter, unreacted sites on the Affi-gel-10 are blocked by addition of 100 ul of 1 M glycine ethyl ester per ml of gel. Applicants found that the antibody-coupled gel routinely contained from 3 to 4 mg of antibody per ml of gel.

Because the 2A3-A1H antibody exhibits such an extremely high affinity for the IL-2 receptor, the receptor yield from the chromatography columns was improved by employing columns prepared with a mixture of MOPC-21 and 2A3-A1H antibody. A total of 3 to 4 mg IgG is still coupled per ml of gel, but only 10-30% of the IgG is composed of 2A3-A1H. The column having both MOPC-21 and 2A3-A1H antibody bound thereto will be referred to as the "2A3-A1H" column.

Prior to use, each gel is washed extensively with PBS and RIPA buffer. The MOPC-21 and 2A3-A1H gel columns are poured in 3 ml syringes that have their open ends closed with a cork and tubing, thereby to enable the columns to be run in either direction. The cell extracts, as prepared in Examples 1 and 2 above, are first applied to the MOPC-21 column at a flow rate of 0.1 ml/min at 4° C. to remove proteins that nonspecifically bind to the mouse IgG. This absorption is repeated once more and then the flow-through from the MOPC-21 column is twice applied to the 2A3-A1H column.

The 2A3-A1H column is then washed with 10 column volumes of PBS-1% Triton X-100, 10 column volumes of RIPA buffer and lastly, 10 column volumes of PBS-1% Triton X-100. Thereafter, the receptor is eluted from the column with 6 M guanidine hydrochloride ("GuHCl") and 0.5% Triton X-100. Eluate fractions in 1.2 ml volume are collected and each fraction is dialyzed against 3 M GuHCl in 0.5% Triton X-100 for four hours. This is followed by dialysis against 1.5 M GuHCl in 0.5% Triton X-100. Final dialysis is performed against PBS containing 0.5% Triton X-100. Aliquots at each stage of the purification are saved for analysis of: biological activity by the above-described soluble receptor assays; protein concentration by fluorescamine assay with bovine serum albumin as a standard, as is well-known in the art; and, protein heterogeneity by polyacrylamide gel electrophoresis with the protein being detected by silver staining, as also described above. From these assays, the IL-2 receptor from the HUT-102 cells was found to have a specific activity of approximately 2,000 fm receptor/ug protein. The specific activity from the PHA-PBL cells was somewhat less.

EXAMPLE 6

Reversed Phase High Performance Liquid Chromatography

The active fractions obtained in Example 5 are pooled for use as the starting material for the HPLC process. These fractions are pumped directly onto a 3.9 mm times 15 cm Vydac C-4 column, which has been previously equilibrated with 0.1 percent TFA in water, at a flow rate of about 1 ml/min with a Waters M-45 A solvent pump (Waters Associates, Millford, Me.). The loaded column is initially washed with 0.1% TFA to remove non-bound components until the absorbence at 214 nm as detected with a Waters Model 441 absorbence detector drops to base line. Elution of bound proteins is accomplished with a linear gradiant of 0.95% acetonitrile in 0.1 percent TFA (v/v) at a rate of 1% per minute. The IL-2 receptor protein was found to elute eluded off the column in the 50 to 55% acetonitrile fractions.

One minute fractions are collected (1 ml) and 50 ul aliquots are removed from each fraction for analysis by polyacrylamide gel electrophoresis followed by silver staining. This technique resulted in the separation of a single band of protein at a molecular weight of 55,000 daltons for the HUT-102 receptor molecule. The PHA-PBL receptor molecule, which eluted at the same position on the HPLC as the HUT-102 receptor molecule, exhibited a single band of protein having a molecular weight of 60,000 daltons.

Aliquots in 50 ul volumes are also removed from the minute fractions for biological assay. The aliquots are dried under vacuum in the presence of 50 ug BSA. The dried residue is dissolved in PBS-2% Triton X-100 for analysis by the soluble receptor assay techniques discussed above. This assay indicated that the IL-2 from HUT-102 receptor had been purified from 1.26 fmole receptor/ug in protein the cell lysate starting material to approximately 21,000 fmole receptor/ug protein after the HPLC purification step. This equates to an increase in purification of the IL-2 receptor of about 16,670 times. The specific activity of the PHA-BPL receptor after the HPLC purification step was found to be approximately 5,000 fmole receptor/ug protein. It is clear from the single protein bands which resulted from the polyacrylamide gel electrophoresis and silver staining of the fractions collected after HPLC, and also from the specific activities of the fractions analyzed by the soluble receptor assays, essential homogeneity of the IL-2 receptor molecule was achieved.

EXAMPLE 7

Amino Acid Sequencing

Purified IL-2 receptor from Example 6 is dried under vacuum to a final volume of approximately 100 ul and then subjected to automated amino terminal Edman degration using an Applied Biosystems Model 470A protein sequencer. Fractions from the sequencing cycles are evaporated to dryness and then resuspended in acetonitrile/$H_2O$ (50:50) before injection into an HPLC column for residue identification.

By the above process, the amino-terminal amino acid sequence for the IL-2 receptor from both the HUT-120 and PHA-PBL cells were found to be the same. The first 15 residues of the N-terminal portion of the IL-2 receptor molecule was determined to be composed of the following sequence: Glu-Leu-Cys-Asp-Asp-Asp-Pro-Pro-Glu-Ile-Pro-His-Ala-Thr-Phe. This amino acid sequence was compared with known protein sequences contained in the National Biomedical Research Foundation protein data base "SEARCH" (January, 1984), and was not significantly homologous to any protein sequence contained in this data base.

As will be apparent to those skilled in the art to which the invention is addressed, the present invention may be carried out by using cell lines, culture media, culture media additives, culture conditions, assays, antibodies, purification techniques, and chromotography columns other than those specifically discussed above without departing from the spirit or essential characteristic of the invention. The particular materials and processes described above are therefore to be considered in all respects as illustrative and not restrictive. The scope of the present invention is as set forth in the appended claims rather than being limited to the examples of the methods and procedures set forth in the foregoing description.

The embodiments of the invention in which an exclusive property of privilege is claimed are defined as follows:

1. A process for producing a homogeneous receptor for interleukin 2, comprising:
    (a) culturing cells capable of expressing interleukin 2 receptor molecules in culture medium;
    (b) harvesting said cells from the culture medium;
    (c) extracting the interleukin 2 receptor molecules from said cells; and
    (d) purifying said interleukin 2 receptor molecules with a reversed phase, high-performance liquid chromatography column containing methyl groups covalently bonded to silica gel whereby the interleukin 2 receptor molecules are retained by the column.

2. The process of claim 1, wherein culturing said interleukin 2 receptor expressing molecules includes culturing T-cells in the presence of an activating agent.

3. The process according to claim 2, wherein said activating agent is a T-cell mitogen.

4. The process according to claim 1, wherein said interleukin 2 receptor expressing cells comprise malignant cells.

5. The process according to claim 4, wherein said malignant cells are T-lymphoma or T-leukemia cells.

6. The process according to claim 1, wherein said interleukin 2 receptor expressing cells comprise normal T-cells.

7. The process of claim 1, wherein the interleukin 2 receptor molecules are eluted from the column with an acetonitrile elution gradient.

8. The process according to claim 1, wherein said receptor molecules are initially partially purified by:
    passing the interleukin 2 receptor containing extract through an affinity chromatography column prior to the reversed phase high-performance liquid chromatography procedure, said column containing a gel substrate to which is bound an antibody highly that specifically binds to an antigenic epitope on the interleukin 2 receptor whereby the interleukin 2 receptor is retained by the chromatography column;
    eluting the retained interleukin 2 receptor from the column; and,
    pooling fractions exhibiting interleukin 2 activity.

9. A process for preparing interleukin 2 receptor in homogeneous form, said process comprising:
    (a) passing a solution of crude interleukin 2 receptor through an affinity chromatography column containing a column substrate to which is bound an antibody 2A3-A1H(ATCC No. HB8555) highly that specifically binds to an antigenic epitope on the interleukin 2 receptor whereby the interleukin 2 receptor is retained by said chromatography column, eluting the bound interleukin 2 receptor from the column, and pooling fractions exhibiting interleukin 2 receptor activity; and
    (b) passing the interleukin 2 receptor containing fractions from step (a) above through a reversed phase, high-performance liquid chromatography column containing methyl groups covalently bonded to silica gel whereby the interleukin 2 receptor is retained by said chromatography column, eluting said chromatography column with an acetonitrile elution gradient, and pooling fractions exhibiting interleukin 2 receptors.

10. The process according to claim 1, wherein said high-performance liquid chromatography column contains four methyl groups covalently bonded to silica gel.

* * * * *

UNITED STATES PATENT AND TRADEMARK OFFICE
CERTIFICATE OF CORRECTION

PATENT NO. : 4,578,335  
DATED : March 25, 1986  
INVENTOR(S) : Urdal et al.

It is certified that error appears in the above-identified patent and that said Letters Patent is hereby corrected as shown below:

At Column 2, under "OTHER PUBLICATIONS," line 9, add:

"A Monoclonal Antibody (Anti-Tac) Reactive With Activated And Functionally Mature Human T Cells; I. Production Of Anti-Tac Monoclonal Antibody And Distribution of Tac (+) Cells", Takashi Uchiyama et al. The Journal Of Immunology, Vol 126, No. 4, 04/81, pp. 1393-1397.

"A Monoclonal Antibody (Anti-Tac) Reactive With Activated And Functionally Mature Human T Cells; II. Expression of Tac Antigen On Antivated Cytotoxic Killer T Cells, Suppressor Cells, And On One of Two Types of Helper T Cells", Takashi Uchiyama et al., The Journal of Immunology, Vol 126, No. 4, 04/81, pp. 1398-1403.

"Blockade Of The Interleukin-2 Receptor By Anti-Tac Antibody: Inhibition Of Human Lymphocyte Activation", Joel M. Depper et al., The Journal Of Immunology, Vol. 131, No. 2, August 1983, pp. 690-696.

"Characterization Of The Human Receptor For T-Cell Growth Factor", Warren J. Leonard et al. Proc. Natl. Acad. Sci. USA, Vol 80, pp. 6957-6961, November 1983 Immunology.

Column 2,   line 20, "homogenity" should be --homogeneity--
                 line 52, "phytohem-agglutinin" should be --phytohemagglutinin--
                 line 53, after "numbers" insert --of--
     Column 4,   line 16, "ion exchanger" should be --ion exchange--
     Column 8,   line 20, "0 to 5" should be --0 to 95--
     Column 9,   line 20, "2mm" should be --2mM--
                 line 30, "pellet n" should be --pellet in--
                 line 48, delete "to"
                 line 51, delete "to"

UNITED STATES PATENT AND TRADEMARK OFFICE
CERTIFICATE OF CORRECTION

PATENT NO. : 4,578,335            Page 2 of 2

DATED : March 25, 1986

INVENTOR(S) : Urdal et al.

It is certified that error appears in the above-identified patent and that said Letters Patent is hereby corrected as shown below:

Column 10,    line 51, delete "a"
                 line 64, "at" should be --as--
Column 11,    line 48, "cupled" should be --coupled--
Column 12,    line 49, "0.95" should be --0-95%--

Column 14,    line 32, "highly that" should be --that highly--
                 line 44, delete "highly" and insert --that--
                 line 45, delete "that" and insert --highly--

Signed and Sealed this

Twenty-seventh Day of December, 1988

*Attest:*

DONALD J. QUIGG

*Attesting Officer*            *Commissioner of Patents and Trademarks*